(12) United States Patent
Zhuang et al.

(10) Patent No.: US 12,011,522 B2
(45) Date of Patent: Jun. 18, 2024

(54) STERILIZATION MODULE AND AIR PURIFIER

(71) Applicant: SHENZHEN YITOA INTELLIGENT INDUSTRIAL CO., LTD, Shenzhen (CN)

(72) Inventors: Junhuang Zhuang, Shenzhen (CN); Shujie Wang, Shenzhen (CN); Zhihong Zheng, Shenzhen (CN)

(73) Assignee: SHENZHEN YITOA INTELLIGENT INDUSTRIAL CO., LTD, Shenzhen (CN)

( * ) Notice: Subject to any disclaimer, the term of this patent is extended or adjusted under 35 U.S.C. 154(b) by 377 days.

(21) Appl. No.: 17/577,717

(22) Filed: Jan. 18, 2022

(65) Prior Publication Data

US 2023/0128358 A1    Apr. 27, 2023

(30) Foreign Application Priority Data

Oct. 21, 2021    (CN) .......................... 202122548300.1

(51) Int. Cl.
*A61L 9/20* (2006.01)
*F21V 7/04* (2006.01)

(52) U.S. Cl.
CPC .................... *A61L 9/20* (2013.01); *F21V 7/04* (2013.01)

(58) Field of Classification Search
CPC .... A61L 9/20; A61L 2209/14; A61L 2209/16; B60H 3/0078
See application file for complete search history.

(56) References Cited

U.S. PATENT DOCUMENTS 11,071,803 B1 *   7/2021   Lan ......................... F21S 8/06

FOREIGN PATENT DOCUMENTS

CN        213373936 U  *  6/2021
DE    112016005664 T5  *  9/2018  ............. A61L 9/205

* cited by examiner

*Primary Examiner* — David E Smith
*Assistant Examiner* — Hsien C Tsai
(74) *Attorney, Agent, or Firm* — Li & Cai Intellectual Property (USA) Office

(57) ABSTRACT

Provided are a sterilization module and an air purifier, which are applied in the field of air sterilization. The sterilization module is applied in the air purifier. The sterilization module includes a frame, a plurality of wave-shaped plates, and at least one sterilizing lamp. The frame is provided with a channel running through the frame from one end to another end. The plurality of wave-shaped plates are arranged at intervals in the channel, where each of the plurality of wave-shaped plates is bent alternately from the one end to the another end of the frame, so as to form an air duct that is wave-shaped between two adjacent wave-shaped plates. The at least one sterilizing lamp is disposed on the wave-shaped plate and used to emit ultraviolet (UV) light towards the air duct.

18 Claims, 7 Drawing Sheets

STERILIZATION MODULE AND AIR PURIFIER

FIELD OF THE DISCLOSURE

The present application relates to the field of air sterilization, and more particularly to a sterilization module and an air purifier.

BACKGROUND OF THE DISCLOSURE

In the existing air purifier with a filter element, bacteria in the air are intercepted by the filter element when passing through the filter element. When the dust holding capacity of the filter element reaches the limit, it is required to replace the filter element, resulting in an increase in cost. However, for an air purifier that is not disposed with a filter element but simply uses plasma and ultraviolet (UV) sterilization manners, the air is insufficiently irradiated because the wind speed is too fast, so that the sterilization rate cannot meet the standard.

SUMMARY OF THE DISCLOSURE

The present application provides a sterilization module and an air purifier, so as to solve the problem in the prior art that the sterilization rate of the air purifier that is not disposed with a filter element but simply uses plasma and UV sterilization manners cannot meet the standard because the wind speed is too fast and the air is insufficiently irradiated.

To solve the foregoing problem, the present application provides a sterilization module, which includes:
  a frame, provided with a channel running through it;
  a plurality of wave-shaped plates, arranged at intervals in the channel, where each wave-shaped plate is bent alternately from one end to another end of the frame, so as to form an air duct that is wave-shaped between two adjacent wave-shaped plates; and
  at least one sterilizing lamp, disposed on the wave-shaped plate and used to emit UV light towards the air duct.

In a possible implementation, the wave-shaped plate is disposed with a reflecting layer which is used to reflect the UV light emitted from the sterilizing lamp.

In a possible implementation, the reflecting layer includes a retro-reflection layer and a diffuse reflection layer that are respectively disposed on two opposite surfaces of two adjacent wave-shaped plates.

In a possible implementation, the wave-shaped plate is provided with a plurality of first strip-shaped protrusions which are arranged in a direction along the one end to the another end of the frame.

In a possible implementation, the wave-shaped plate is provided with a plurality of second strip-shaped protrusions which are arranged in a direction along one side of the wave-shaped plate connected to the frame to another side of the wave-shaped plate connected to the frame, so that a part where the first strip-shaped protrusions and the second strip-shaped protrusions overlap with each other is arc-shaped.

In a possible implementation, multiple ones of the sterilizing lamps are arranged at intervals at at least one of a trough and a crest on a surface of the wave-shaped plate that faces the air duct.

In a possible implementation, the sterilizing lamps include UVA lamps and UVC lamps that are alternately arranged in a direction along one side of the wave-shaped plate connected to the frame to another side of the wave-shaped plate connected to the frame.

In a possible implementation, the sterilization module further includes a circuit board, where the at least one sterilizing lamp is disposed on the circuit board;
  wherein each of the plurality of wave-shaped plates has a groove arranged in a direction along one side of the wave-shaped plate connected to the frame to another side of the wave-shaped plate connected to the frame, and the groove is used to accommodate the circuit board.

In a possible implementation, a concave portion is disposed at both of the two ends of the groove on the wave-shaped plate, a surface of the wave-shaped plate that faces away from the groove is provided with a convex portion, and the convex portion and the concave portion face away from each other; and
  when the convex portion of one wave-shaped plate is inserted into the concave portion of another wave-shaped plate, the circuit board is pressed between the concave portion and the convex portion.

The present application further provides an air purifier, which includes the sterilization module provided in any of the foregoing embodiments.

The present application has the following beneficial effects: In the sterilization module provided by the present application, the plurality of wave-shaped plates are arranged at intervals in the frame, the air duct that is wave-shaped is formed between two adjacent wave-shaped plates, and each of the plurality of wave-shaped plates is disposed with the sterilizing lamp that can emit UV light. During use, when passing through the air ducts that are wave-shaped in the frame, the air changes its flow direction many times, thus reducing a wind speed without decreasing an air volume, and further prolonging a stay of the air in the air ducts while extending an air circulation path. In this way, the air can be sufficiently irradiated by the UV light emitted from the sterilizing lamps, thus improving a sterilization rate. Moreover, the air ducts that are wave-shaped can avoid direct leakage of the UV light, thus improving the safety.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

To describe the technical solutions in the embodiments of the present application more clearly, the following briefly introduces the accompanying drawings required in the embodiments. It should be noted that, the accompanying drawings in the following description show merely some embodiments of the present application and should not be regarded as limitations to the scope. Those of ordinary skill in the art can still derive other related drawings from these accompanying drawings without creative efforts.

MEANINGS OF NUMERALS

Figure 1:
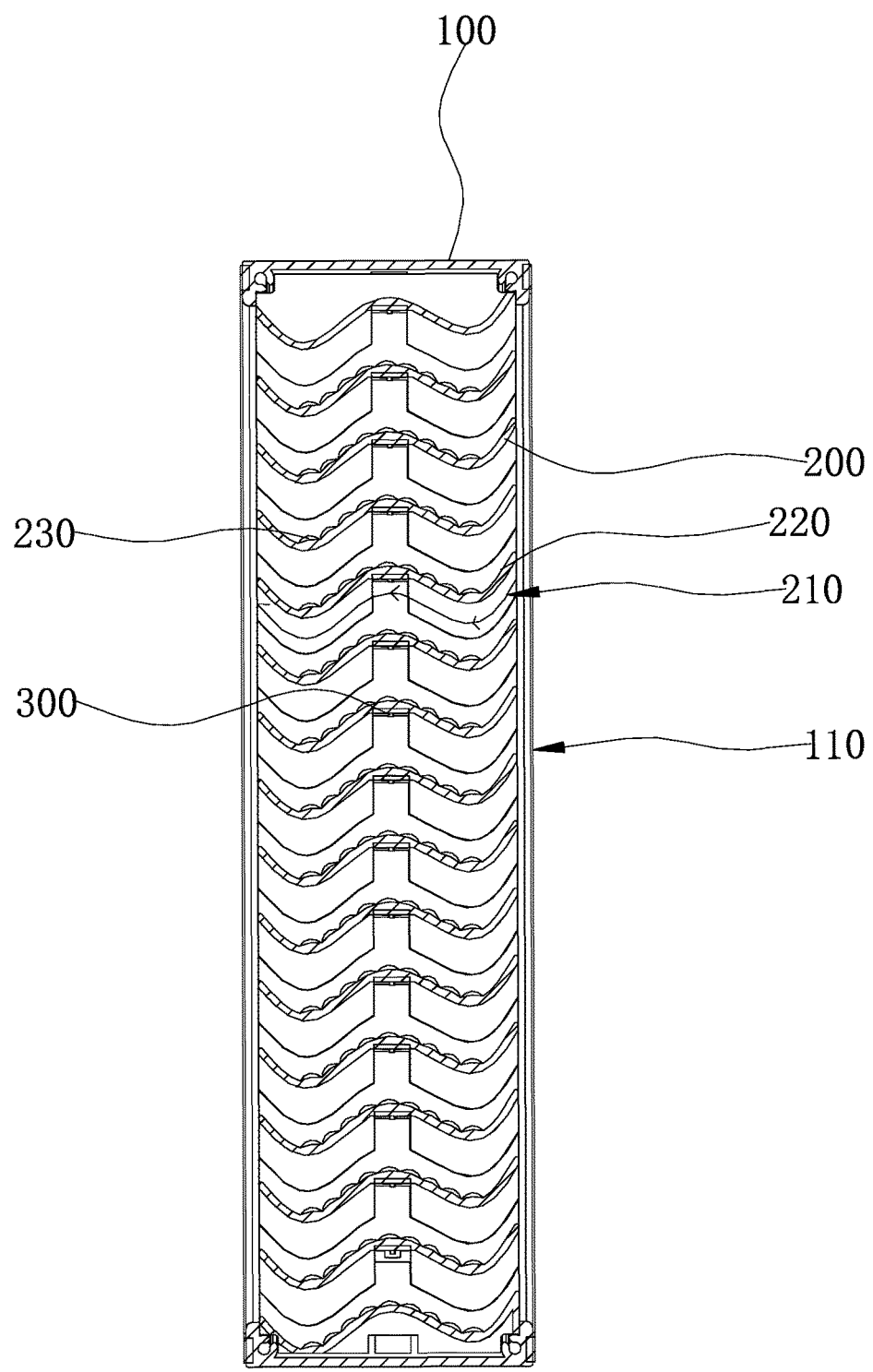
FIG. 1 is a schematic sectional structural diagram of a sterilization module provided in an embodiment of the present utility model.

100. Frame; 110. Channel; 200. Wave-shaped plate; 210. Air duct; 220. Reflecting layer; 230. First strip-shaped protrusion; 240. Second strip-shaped protrusion; 250. Through hole; 260. Convex portion; 270. Concave portion; 280. Groove; 300. Sterilizing lamp; 310. Circuit board

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

The embodiments of the present application are described in detail below. Examples of these embodiments are shown in the accompanying drawings, in which the same or similar numerals indicate the same or similar elements or elements with the same or similar functions. The embodiments described below with reference to the accompanying drawings are exemplary and only used to explain the present application, but cannot be understood as limitations to the present application.

In the description of the present application, it should be noted that, the orientations or positional relationships indicated by the terms "center", "longitudinal", "transverse", "length", "width", "thickness", "upper", "lower", "front", "rear", "left", "right", "vertical", "horizontal", "top", "bottom", "inner", "outer", "clockwise", "counterclockwise", "axial", "radial", "circumferential", etc. are based on the orientations or positional relationships shown in the accompanying drawings, and are only used for the convenience of describing the present application and simplifying the description, rather than indicating or implying that the denoted device or element must have a specific orientation or be constructed and operated in a specific orientation. Therefore, these terms cannot be understood as limitations to the present application.

In addition, the terms "first" and "second" are only used for descriptive purposes, and cannot be understood as indicating or implying relative importance or implicitly indicating the number of indicated technical features. Thus, the features defined with "first" and "second" may explicitly or implicitly include one or more of these features. In the description of this present application, "multiple" means two or more than two, unless otherwise specifically defined.

In the present application, unless expressly stipulated and limited otherwise, the terms "installation", "connected", "joined", "fixed" and other terms should be understood in a broad sense. For example, these terms may indicate a fixed connection or removable connection, or integration into a whole; or indicate mechanical connection or electrical connection; or mean direct connection or indirect connection via an intermediate medium, or internal communication or interaction between two components. For those of ordinary skill in the art, the specific meanings of the above terms in the present application can be understood according to specific situations.

In the present application, unless expressly stipulated and defined otherwise, the first feature "above" or "below" the second feature may be that the first and second features are in direct contact, or in indirect contact via an intermediate medium. Moreover, the first feature "above", "over" and "on" the second feature may mean that the first feature is directly above or obliquely above the second feature, or simply mean that the level of the first feature is higher than that of the second feature. The first feature "below", "under" and "beneath" the second feature may mean that the first feature is directly below or obliquely below the second feature, or simply mean that the level of the first feature is lower than the second feature.

First Embodiment

Figure 2:
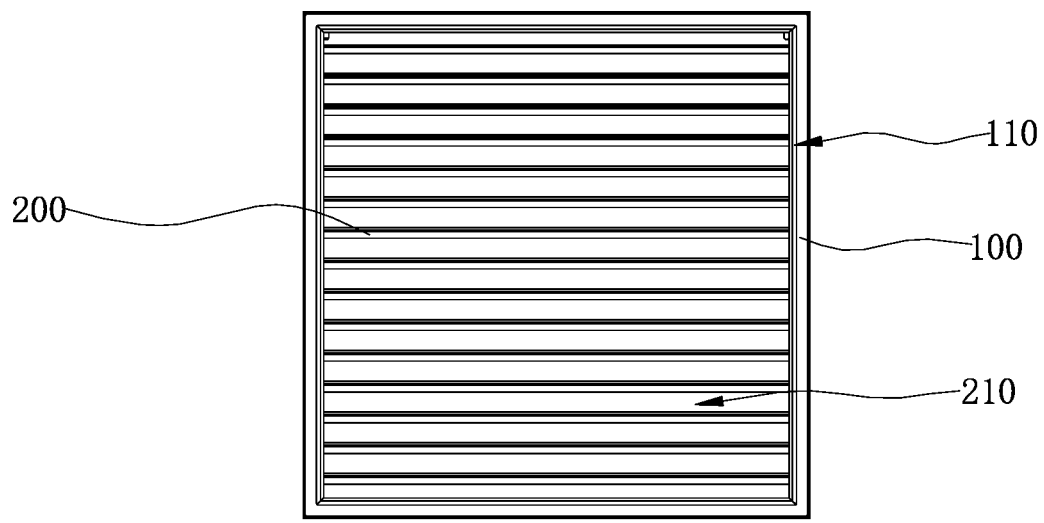
FIG. 2 is a schematic structural diagram of the sterilization module provided in an embodiment of the present utility model from one viewing angle.
Figure 3:
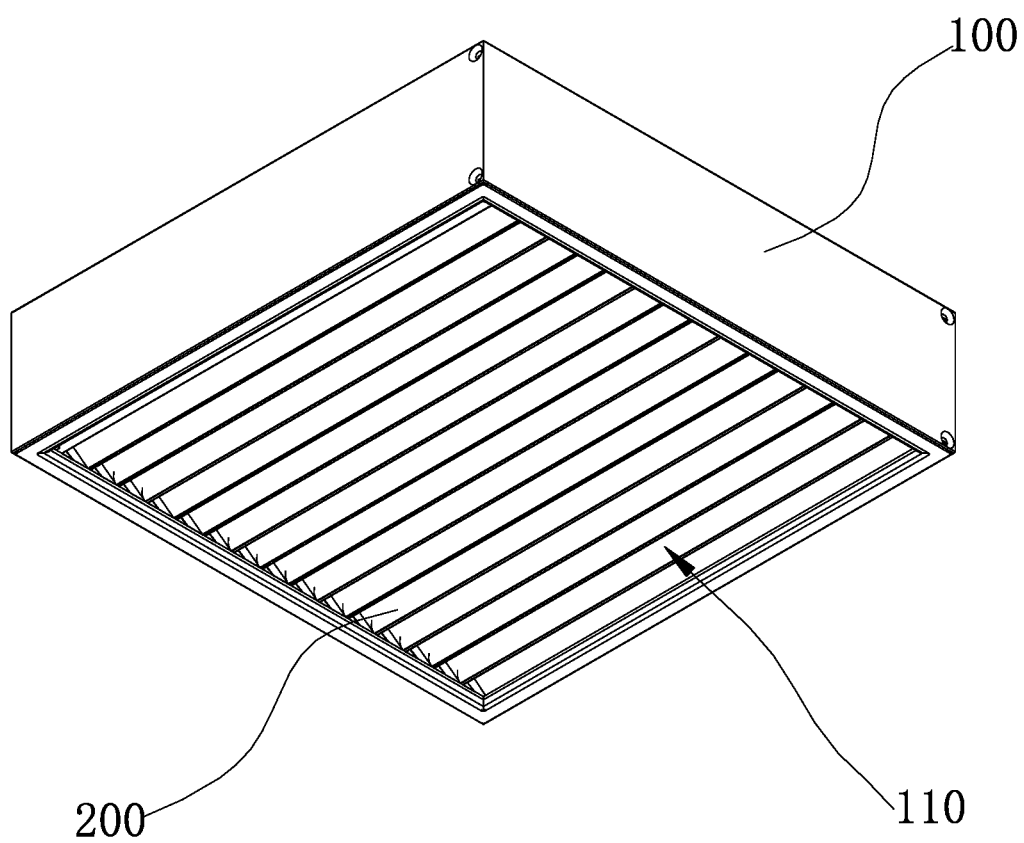
FIG. 3 is a schematic structural diagram of the sterilization module provided in an embodiment of the present utility model from another viewing angle.

Referring to FIGS. 1, 2, and 3, this embodiment provides a sterilization module applied in an air purifier, where the sterilization module includes a frame 100, a plurality of wave-shaped plates 200, and at least one sterilizing lamp 300. The frame 100 is provided with a channel 110 running through the frame 100 from the one end to the another end. The plurality of wave-shaped plates 200 is arranged at intervals in the channel 110, where each of the plurality of wave-shaped plates 200 is bent alternately from the one end to the another end of the frame 100, so as to form an air duct 210 that is wave-shaped between two adjacent wave-shaped plates 200. The at least one sterilizing lamp 300 is disposed on the wave-shaped plate 200 and used to emit UV light towards the air duct 210.

In the sterilization module provided in the embodiment of the present application, multiple wave-shaped plates 200 are arranged at intervals within the frame 100, an air duct 210 that is wave-shaped is formed between two adjacent wave-shaped plates 200, and the wave-shaped plate 200 is disposed with a sterilizing lamp 300 that can emit UV light. Therefore, during use, when passing through the air ducts 210 that are wave-shaped in the frame 100, the air changes its flow direction many times, thus reducing the wind speed without decreasing the air volume, and further prolonging the stay of the air in the air ducts 210 while extending the air circulation path. In this way, the air can be sufficiently irradiated by the UV light emitted from the sterilizing lamp 300, thus improving the sterilization rate. Moreover, the air ducts that are wave-shaped 210 that are wave-shaped can avoid direct leakage of the UV light, thus improving the safety.

According to the scenario of use and available space, the number, length, and width of the wave-shaped plates 200 and the number of folds thereon can be changed, and the number of the sterilizing lamps 300 and the space therebetween can also be changed. In addition, the sectional shape of the wave-shaped plate 200 is not limited to symmetrical waves, and may also be asymmetrical waves.

It should be noted that, an application scenario of the sterilization module provided by this embodiment is not limited to an air purifier, and the sterilization module can also be applied in an air conditioner, a fresh air ventilator, a vehicle ventilation system, or other scenarios. The sterilization module can be used in combination with an apparatus that can supply an air pressure, where the apparatus that can supply an air pressure includes, but is not limited to, an axial fan, a cross-flow fan, a centrifugal fan, or the like.

Second Embodiment

Figure 4:
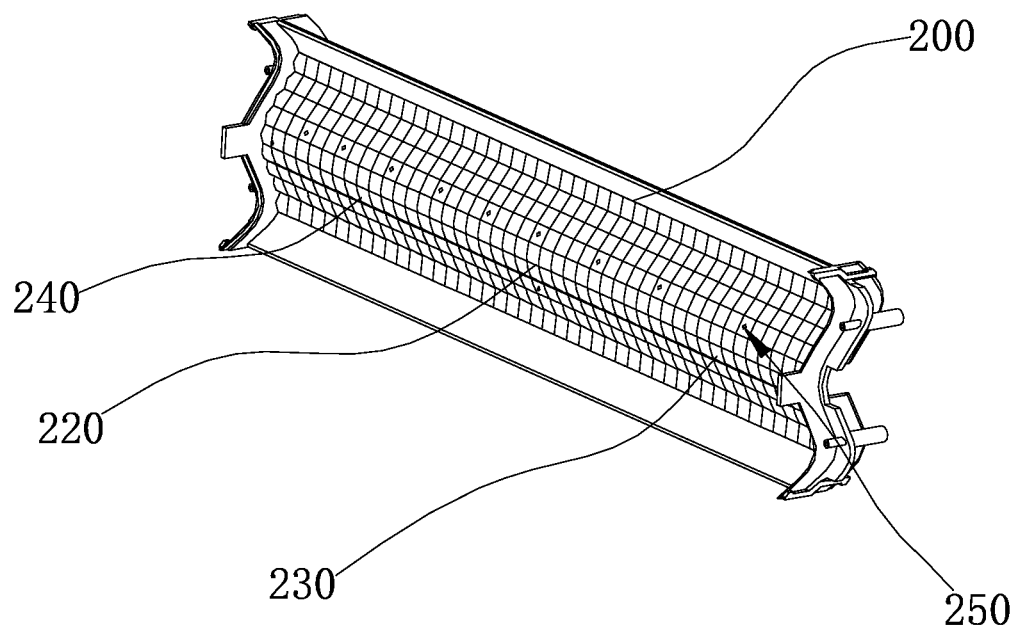
FIG. 4 is a schematic structural diagram of a wave-shaped plate of the sterilization module provided in an embodiment of the present utility model from one viewing angle.

As shown in FIGS. 1 and 4, based on the first embodiment, this embodiment provides an arrangement manner of a reflecting layer 220. The wave-shaped plate 200 is disposed with a reflecting layer 220 which is used to reflect the UV light emitted from the sterilizing lamp 300.

Specifically, by arrangement of the reflecting layer 220 on the wave-shaped plate 200, the UV light emitted from the sterilizing lamp 300 can be reflected many times in the air duct 210 that is wave-shaped, so that the air duct 210 is filled with UV energy, thus improving utilization of the UV light and further improving the sterilization effect.

In the foregoing embodiment, alternatively, the reflecting layer 220 includes a retro-reflection layer and a diffuse reflection layer that are respectively disposed on two opposite surfaces of two adjacent wave-shaped plates 200.

Specifically, by arranging the retro-reflection layer and the diffuse reflection layer respectively on two opposite surfaces of two adjacent wave-shaped plates 200, the UV light emitted from the sterilizing lamp 300 can be retro-reflected back into the air duct 210 during reflection in the air duct 210, so that the UV light at an air inlet and outlet of the air duct 210 is avoided from being directly reflected out of the air duct 210, thus increasing the number of reflections of the UV light and improving the utilization of the UV light.

Third Embodiment

Figure 5:
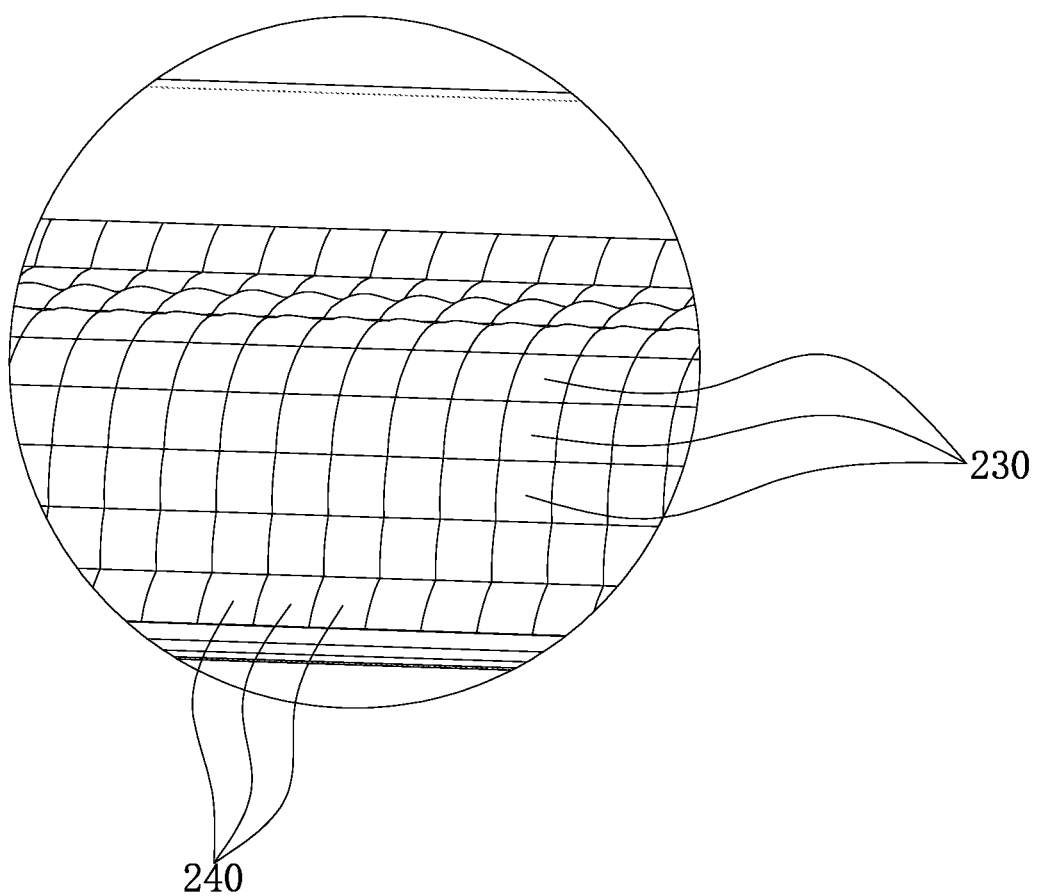
FIG. 5 is a schematic partially enlarged structural diagram of a wave-shaped plate of the sterilization module provided in an embodiment of the present utility model from one viewing angle.

As shown in FIGS. 1, 4, and 5, based on the first or second embodiment, this embodiment provides a design manner of the wave-shaped plate 200. The wave-shaped plate 200 is provided with a plurality of first strip-shaped protrusions 230 which are arranged in a direction along the one end to the another end of the frame 100.

Specifically, a plurality of first strip-shaped protrusions 230 is arranged on the wave-shaped plate 200 in a direction along the one end to the another end of the frame 100, so that a turbulent flow cyclone can be produced when the air passes through the air duct 210. Thus, the wind speed is reduced, and the passing air can be sufficiently irradiated by the sterilizing lamp 300, further improving the sterilization effect. Moreover, the arrangement of the first strip-shaped protrusions 230 enlarges the surface area of the reflecting layer 220 of the wave-shaped plate 200, and increases the reflection angles, so that the UV light can be fully distributed throughout the air duct 210.

As shown in FIGS. 1, 4, and 5, in the foregoing embodiments, alternatively, the wave-shaped plate 200 is provided with a plurality of second strip-shaped protrusions 240 which are arranged in a direction along one side of the wave-shaped plate 200 connected to the frame 100 to another side of the wave-shaped plate 200 connected to the frame 100, so that a part where the first strip-shaped protrusions 230 and the second strip-shaped protrusions 240 overlap with each other is arc-shaped.

Specifically, a plurality of second strip-shaped protrusions 240 arranged in a direction along one side of the wave-shaped plate 200 connected to the frame 100 to another side of the wave-shaped plate 200 connected to the frame 100 is provided on the wave-shaped plate 200, and a part where the first strip-shaped protrusions 230 and the second strip-shaped protrusions 240 overlap with each other is arc-shaped, so that more turbulent flow cyclones can be produced when the air passes through the air duct 210. Thus, the wind speed is further reduced, and the passing air can be more sufficiently irradiated, further improving the sterilization effect. The arc-shaped reflecting layer 220 can increase the UV light reflection angles, so that the UV light can be evenly distributed throughout the air duct 210.

Fourth Embodiment

Figure 6:
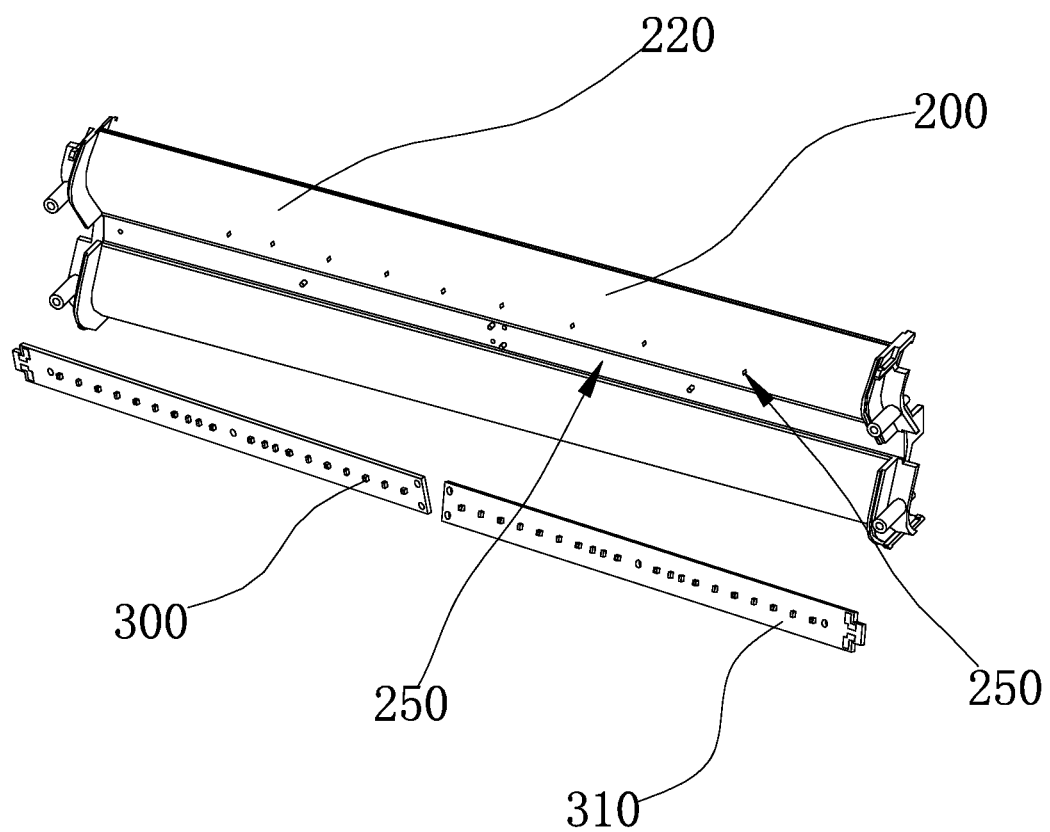
FIG. 6 is a schematic exploded structural diagram of the wave-shaped plate of the sterilization module provided in an embodiment of the present utility model from another viewing angle.

As shown in FIGS. 1 and 6, based on the first embodiment to the third embodiment, this embodiment further limits the technical solution. Multiple ones of the sterilizing lamps are 300 are arranged at intervals at at least one of a trough and a crest on a surface of the wave-shaped plate 200 that faces the air duct 210.

Specifically, when multiple ones of the sterilizing lamps 300 are arranged at intervals at at least one of a trough and a crest, the UV light emitted from the sterilizing lamps 300 can be reflected by a reflective layer 220 of an opposite wave-shaped plate 200 towards a direction away from the sterilizing lamps 300, so that the UV light is evenly distributed in the air duct 210. When multiple ones of the sterilizing lamps 300 are arranged at intervals at at least one of a trough and a crest, the UV light emitted from the sterilizing lamps 300 can be reflected by a reflective layer 220 of an opposite wave-shaped plate 200 towards the sterilizing lamps 300, so that the UV light is concentrated in the air duct 210 near the sterilizing lamps 300. Therefore, the plurality of sterilizing lamps 300 may be arranged at intervals at the trough and/or crest on a surface of the wave-shaped plate 200 that faces the air duct 210 according to actual situations, so as to meet different demands of a user.

In the foregoing embodiments, alternatively, the sterilizing lamps 300 include UVA lamps and UVC lamps that are alternately arranged in a direction along one side of the wave-shaped plate 200 connected to the frame 100 to another side of the wave-shaped plate 200 connected to the frame 100.

Specifically, UV (full name in English: ultraviolet) is the abbreviation for ultraviolet light. The UVA (full name in English: ultraviolet A) lamps can produce UV light with long wavelengths from 365 nm to 405 nm, while the UVC (full name in English: ultraviolet C) lamps can produce UV light with short wavelengths from 200 nm to 275 nm; and the UV light with such two wavelengths has different effects on bacteria, viruses and other microorganisms. The UV light produced by the UVA lamps has a relatively long wavelength and strong penetrating power, and can damage the cell walls of bacterial cells, thus reducing the activity of bacteria. The UV light produced by the UVC lamps has a relatively short wavelength and weak penetrating power, but can damage the DNA of the bacteria, thus completely killing the bacteria. Therefore, with the help of the UV light produced by the UVA lamps, the UV light produced by the UVC lamps can more easily penetrate the bacteria, thus improving the sterilization ability. By alternate arrangement of the UVA and UVC lamps in a direction along one side of the wave-shaped plate 200 connected to the frame 100 to another side of the wave-shaped plate 200 connected to the frame 100, the UV light with two different wavelengths respectively produced by the UVA and UVC lamps can be more evenly distributed in the air duct 210, thus achieving a better sterilization effect.

As shown in FIGS. 4 and 6, the wave-shaped plate 200 may be provided with through holes 250 that enable communication between two adjacent air ducts 210. When air passes through the air duct 210, because through holes 250 that enable communication between two adjacent air ducts 210 are provided on the wave-shaped plate 200, some air can reach the adjacent air duct 210 via the through holes 250, thus producing more turbulent flow cyclones and reducing the wind speed. In this way, the air can be sufficiently irradiated by the UV light emitted from the sterilizing lamps 300, thus improving the sterilization rate.

Figure 7:
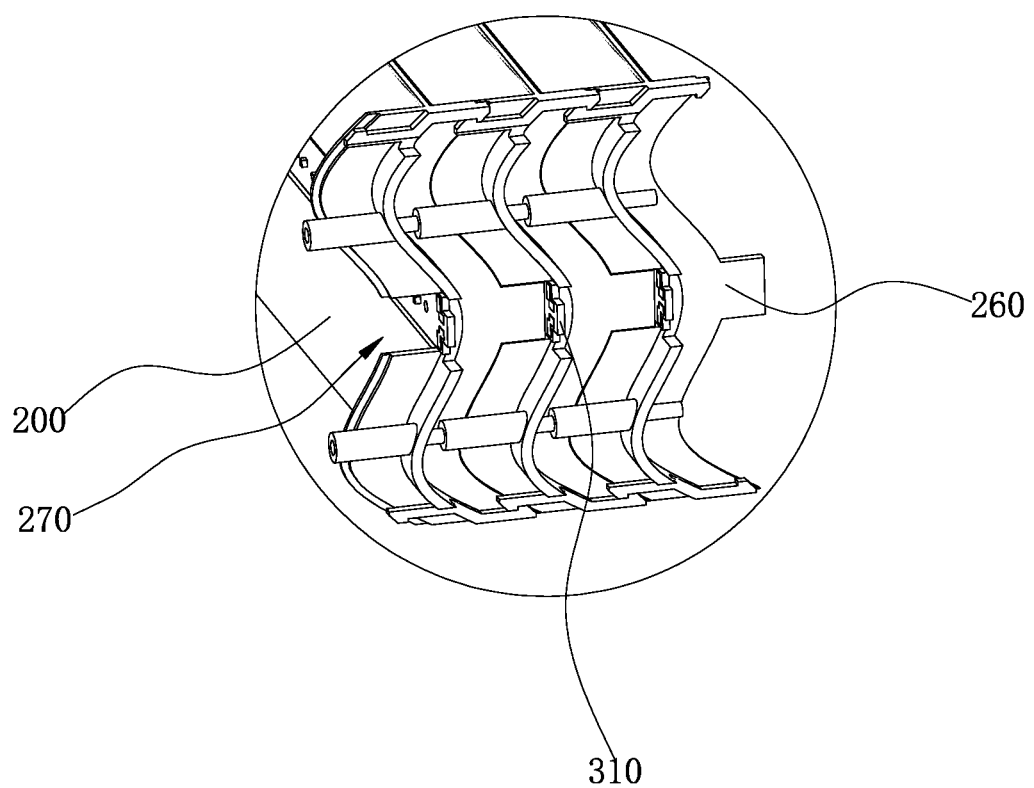
FIG. 7 is a schematic partially enlarged structural diagram showing joining of two adjacent wave-shaped plates of the sterilization module provided in an embodiment of the present utility model.

As shown in FIGS. 6 and 7, in the foregoing embodiments, alternatively, the sterilization module further includes a circuit board 310, and the at least one sterilizing lamp 300 is disposed on the circuit board 310. Each of the plurality of wave-shaped plates has a groove arranged in a direction along one side of the wave-shaped plate 200 connected to the frame 100 to another side of the wave-shaped plate 200 connected to the frame 100, and the groove 280 is used to accommodate the circuit board 310.

Specifically, by arranging the sterilizing lamp 300 on the circuit board 310 and mounting the circuit board 310 in the groove 280, the sterilizing lamp 300 can be secured on the wave-shaped plate 200, and the fitting manner between the circuit board 310 and the groove 280 can achieve a foolproofing effect.

As shown in FIGS. 6 and 7, in the foregoing embodiments, alternatively, a concave portion 270 is disposed at both of the two ends of the groove 280 on the wave-shaped plate 200, and a surface of the wave-shaped plate 200 that faces away from the groove 280 is provided with a convex portion 260, where the convex portion 260 and the concave portion 270 face away from each other. When the convex portion 260 of one wave-shaped plate 200 is inserted into the concave portion 270 of another wave-shaped plate 200, the circuit board 310 is pressed between the concave portion 270 and the convex portion 260.

Specifically, two adjacent wave-shaped plates 200 can be detachably connected by joining between the convex portion 260 and the concave portion 270. Moreover, the circuit board 310 can be sandwiched between the concave portion 270 and the convex portion 260, so as to be secured in the groove 280. In addition, the shape of the air duct 210 and the wind speed therein can be changed by changing the shape of the wave-shaped plate 200, thus adjusting the sterilization effect and meeting different demands of the user.

Fifth Embodiment

Another embodiment of the present application provides an air purifier, which includes the sterilization module in any of the foregoing embodiments.

The air purifier provided in the embodiment of the present application has the sterilization module provided in any of the foregoing embodiments, and thus has all beneficial effects of the sterilization module provided in any of the foregoing embodiments, so the details are not described in detail herein.

In the description of the present specification, the reference terms "one embodiment", "some embodiments", "example", "specific example", "some examples" and the like mean that specific characteristics, structures, materials or features described with reference to the embodiments or examples are included in at least one embodiment or example of the present application. In the present specification, the schematic description of the above terms does not have to be directed to the same embodiment or example. Furthermore, the described specific characteristics, structures, materials, or features may be combined in a suitable manner in any one or more of the embodiments or examples. In addition, those skilled in the art can integrate and combine different embodiments or examples and features of the different embodiments or examples described in the present specification, without contradicting each other.

Although the embodiments of the present application have been shown and described above, it can be understood that the foregoing embodiments are exemplary only and should not be construed as limiting the present application. Those of ordinary skill in the art can make changes, modifications, substitutions, and modifications to the above-mentioned embodiments within the scope of the present application.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:
1. A sterilization module, comprising:
a frame, provided with a channel running through the frame from the one end to the another end;
a plurality of wave-shaped plates, arranged at intervals in the channel, wherein each of the plurality of wave-shaped plates is bent alternately from the one end to the another end of the frame, so as to form an air duct that is wave-shaped between two adjacent wave-shaped plates; and at least one sterilizing lamp, disposed on the wave-shaped plate and used to emit ultraviolet (UV) light towards the air duct.

2. The sterilization module according to claim 1, wherein the wave-shaped plate is disposed with a reflecting layer which is used to reflect the UV light emitted from the sterilizing lamp.

3. The sterilization module according to claim 2, wherein the reflecting layer includes a retro-reflection layer and a diffuse reflection layer that are respectively disposed on two opposite surfaces of two adjacent wave-shaped plates.

4. The sterilization module according to claim 1, wherein the wave-shaped plate has a plurality of first strip-shaped protrusions which are arranged in a direction along the one end to the another end of the frame.

5. The sterilization module according to claim 4, wherein the wave-shaped plate has a plurality of second strip-shaped protrusions which are arranged in a direction along one side of the wave-shaped plate connected to the frame to another side of the wave-shaped plate connected to the frame, so that a part where the first strip-shaped protrusion and the second strip-shaped protrusion overlap with each other is arc-shaped.

6. The sterilization module according to claim 1, wherein multiple ones of the sterilizing lamps are arranged at intervals at at least one of a trough and a crest on a surface of the wave-shaped plate that faces the air duct.

7. The sterilization module according to claim 6, wherein the sterilizing lamp includes UVA lamps and UVC lamps that are alternately arranged in a direction along one side of the wave-shaped plate connected to the frame to another side of the wave-shaped plate connected to the frame.

8. The sterilization module according to claim 1, further comprising:

a circuit board, wherein the at least one sterilizing lamp is disposed on the circuit board;

wherein each of the plurality of wave-shaped plates has a groove arranged in a direction along one side of the wave-shaped plate connected to the frame to another side of the wave-shaped plate connected to the frame, and the groove is used to accommodate the circuit board.

9. The sterilization module according to claim 8, wherein a concave portion is arranged at each of two ends of the groove on the wave-shaped plate, a surface of the wave-shaped plate that faces away from the groove is provided with a convex portion, and the convex portion and the concave portion are arranged back to each other; and wherein, when the convex portion of one wave-shaped plate is inserted into the concave portion of another wave-shaped plate, the circuit board is pressed between the concave portion and the convex portion.

10. An air purifier, comprising the sterilization module according to claim 1.

11. An air purifier, comprising the sterilization module according to claim 2.

12. An air purifier, comprising the sterilization module according to claim 3.

13. An air purifier, comprising the sterilization module according to claim 4.

14. An air purifier, comprising the sterilization module according to claim 5.

15. An air purifier, comprising the sterilization module according to claim 6.

16. An air purifier, comprising the sterilization module according to claim 7.

17. An air purifier, comprising the sterilization module according to claim 8.

18. An air purifier, comprising the sterilization module according to claim 9.

* * * * *